(12) United States Patent
Je et al.

(10) Patent No.: US 8,293,381 B2
(45) Date of Patent: Oct. 23, 2012

(54) ANTHRACENE DERIVATIVE AND ORGANIC ELECTROLUMINESCENT DEVICE USING THE SAME

(75) Inventors: Jong-Tae Je, Cheongju (KR); Sug-Kwang Hwang, Cheongwon-gun (KR); Sung-Hoon Kim, Jeonju (KR); Seung-Hyuck Choi, Busan (KR); Seon-Keun Yoo, Jeungpyeong-gun (KR)

(73) Assignee: SFC Co., Ltd., Cheongwon-Kun, Chungbuk (KR)

( * ) Notice: Subject to any disclaimer, the term of this patent is extended or adjusted under 35 U.S.C. 154(b) by 400 days.

(21) Appl. No.: 11/948,196

(22) Filed: Nov. 30, 2007

(65) Prior Publication Data

US 2008/0152950 A1    Jun. 26, 2008

(30) Foreign Application Priority Data

Nov. 30, 2006    (KR) .................. 10-2006-0119531

(51) Int. Cl.
*H01L 51/50* (2006.01)
(52) U.S. Cl. ........ 428/690; 428/917; 313/504; 313/505; 313/506; 257/40; 257/E51.05; 257/E51.026; 257/E51.032; 585/26; 585/27
(58) Field of Classification Search .......... 428/690, 428/917; 313/504, 505, 506; 257/E51.05, 257/E51.026, E51.032; 585/26, 27
See application file for complete search history.

(56) References Cited

U.S. PATENT DOCUMENTS

2004/0018383 A1 *    1/2004    Aziz et al. .................... 428/690

FOREIGN PATENT DOCUMENTS

JP    2003-146951    *    5/2003

* cited by examiner

*Primary Examiner* — Jennifer Chriss
*Assistant Examiner* — Gregory Clark
(74) *Attorney, Agent, or Firm* — Edwards Wildman Palmer LLP (57) ABSTRACT

An anthracene derivative and an organic electroluminescent device using the same are provided. More specifically, provided are an anthracene derivative represented by Formula 1:

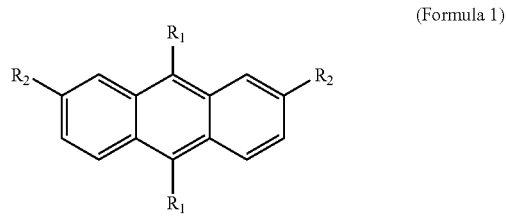

(Formula 1)

wherein each $R_1$ is aryl; and
each $R_2$ is independently $C_6$-$C_{20}$ aryl or $C_3$-$C_{19}$ heteroaryl, which are unsubstituted or substituted with one or more substituents selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl, $C_3$-$C_{19}$ heteroaryl and hydrogen; and an organic electroluminescent device using the same.

The present invention can provide an organic electroluminescent device having excellent power and luminance efficiencies in conjunction with a long service life.

3 Claims, 5 Drawing Sheets

ANTHRACENE DERIVATIVE AND ORGANIC ELECTROLUMINESCENT DEVICE USING THE SAME

CROSS-REFERENCE TO RELATED APPLICATION

This application claims under 35 U.S.C. 119(a) the benefit of Korean Patent Application No. 10-2006-0119531 filed on Nov. 30, 2006, the entire contents of which are incorporated herein by reference.

BACKGROUND

1. Technical Field

The present invention relates to an anthracene derivative and an organic electroluminescent device using the same. More specifically, the present invention relates to an anthracene derivative which enables production of an organic electroluminescent device having excellent power and luminance efficiencies and a long service life, and an organic electroluminescent device using the same.

2. Background Art

An organic electroluminescent device (hereinafter, referred to as "organic EL device") is an active light-emitting display device taking advantage of the phenomenon that light of a particular wavelength is emitted with the exciton transition from an exited state to a ground state in energy level, after formation of excitons from recombination of electrons and holes following the injection of electrons and holes into a fluorescent or phosphorescent organic compound thin film (hereinafter, referred to as "organic film") formed between a first electrode for hole injection (anode) and a second electrode for electron injection (cathode). The organic EL device has various advantages such as the feasibility of weight reduction, simple structure using small numbers of components and parts, simplified manufacturing process, fast response speed, wide viewing angle with high definition, and the like. Further, the organic EL device enables perfect realization of a high-fidelity moving image, the feasibility of high-color purity in conjunction with ultra-slimness, compactness and lightweight in consideration of weight and size, and low power consumption and low driving voltage. That is, organic EL devices have electrical properties suitable for use in portable electronic devices and instruments.

Representative examples of earlier organic EL devices include those having a monolayer structure disclosed in patents issued to Gurnee (U.S. Pat. Nos. 3,172,862 and 3,173,050) in 1969. However, these devices suffer from difficulty in practical application thereof, due to a need for an excessive driving voltage of 100 V or higher. In order to solve such a problem, a multilayer organic EL device having a significantly low driving voltage of about 6 to 14 V was proposed by Tang et al (Eastman Kodak Co.) in 1987 (C. W. Tang et al., *Appl. Phys. Let.*, 51, 913 (1987); *J. Applied Phys.*, 65, 3610 (1989); and U.S. Pat. No. 4,356,429). Currently, there is a continuing trend toward the development of organic EL devices having a variety of functional stack structures including a hole-injection layer, a hole-transport layer, an electron-transport layer and an electron-injection layer.

Meanwhile, conventional organic EL devices employ anthracene and its derivative for a variety of desired applications. For example, there have been proposed techniques of using 9,10-di(2-naphthyl)anthracene, also known as "ADN" (U.S. Pat. No. 5,935,721), 9-naphthyl-10-phenylanthracene derivatives (U.S. Pat. Application Publication No. 2006/0014046 A1) and 9-biphenyl-10-naphthylanthracene derivatives (WO 2005/080527) as a host material of a light-emitting layer, and a technique of improving a service life of an organic EL device via use of bis-anthracene as a light-emitting layer material (U.S. Pat. No. 6,534,199). Further, a technique of using an anthracene derivative in a hole-transport layer (HTL) has been also suggested (U.S. Pat. Nos. 6,465,115 and 5,759,444). Further, there are also known various uses and applications of anthracene and anthracene derivatives in organic EL devices.

As discussed above, even though a great deal of research and study has been made on introduction of anthracene in the organic EL device, prior art technologies do not sufficiently satisfy desired properties such as luminance, efficiency, driving stability and lifespan. Therefore, there is an urgent need for development of various techniques capable of solving such problems. Particularly, in a host-guest system which is based on an energy transfer principle for doping a host of a light-emitting layer with a dopant, there is a need for intense study and research on novel anthracene derivatives as a host material of the light-emitting layer.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Therefore, the present invention has been made in view of the above problems, and it is an object of the present invention to provide an anthracene derivative having excellent power and luminance efficiencies and a long service life.

It is another object of the present invention to provide an organic electroluminescent device using the same anthracene derivative.

In accordance with an aspect of the present invention, the above and other objects can be accomplished by the provision of an anthracene derivative represented by Formula 1 below:

(Formula 1)

wherein each $R_1$ is aryl; and each $R_2$ is independently $C_6$-$C_{20}$ aryl or $C_3$-$C_{19}$ heteroaryl, which are unsubstituted or substituted with one or more substituents selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl, $C_3$-$C_{19}$ heteroaryl and hydrogen.

In accordance with another aspect of the present invention, there is provided an organic electroluminescent device comprising an anode; a cathode; and a layer containing an anthracene derivative of Formula 1 interposed between the anode and the cathode.

DETAILED DESCRIPTION

Hereinafter, reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention is the result of intensive investigations to improve properties such as luminance, efficiency, driving stability and lifespan of an anthracene derivative which has been widely used as a host material of conventional light-emitting layers. More particularly, the present invention has been completed based on the fact that anthracene derivatives represented by Formula 1 have excellent power and luminance efficiencies and a long lifespan.

Accordingly, the present invention provides an anthracene derivative represented by Formula 1:

(Formula 1)

wherein each $R_1$ is aryl; and each $R_2$ is independently $C_6$-$C_{20}$ aryl or $C_3$-$C_{19}$ heteroaryl, which are unsubstituted or substituted with one or more substituents selected from the group consisting of $C_1$-$C_{10}$ alkyl, $C_1$-$C_{10}$ alkoxy, cyano, $C_1$-$C_{10}$ alkylamino, $C_1$-$C_{10}$ alkylsilyl, halogen, $C_6$-$C_{10}$ aryl, $C_6$-$C_{10}$ aryloxy, $C_6$-$C_{10}$ arylamino, $C_6$-$C_{10}$ arylsilyl, $C_3$-$C_{19}$ heteroaryl and hydrogen.

The anthracene derivative in accordance with the present invention has a structure which carries aryl groups at the 9- and 10-positions of the anthracene skeleton and additional substituents at 2- and 7-positions. A conventional anthracene derivative has substituents at 2- and 6-positions, whereas the anthracene derivative of the present invention has substituents at 2- and 7-positions.

In Formula 1, $R_1$ is preferably phenyl.

Examples of the alkyl group which is used as the substituent in the compound of the present invention may include methyl, ethyl, propyl, isobutyl, sec-butyl, tert-butyl, pentyl, iso-amyl, hexyl, and the like. At least one hydrogen atom in the alkyl group may be substituted by halogen, hydroxy, nitro, cyano, silyl (herein, it is called alkylsilyl), substituted or unsubstituted amino (e.g. —NH$_2$, —NH(R), or —N(R')(R") with each of R' and R" independently being $C_1$-$C_{10}$ alkyl, and it is called alkylamino herein), amidino, hydrazine, hydrazone, carboxyl, sulfonic acid, phosphoric acid, $C_1$-$C_{20}$ alkyl, $C_1$-$C_{20}$ halogenated alkyl, $C_1$-$C_{20}$ alkenyl, $C_1$-$C_{20}$ alkynyl, $C_1$-$C_{20}$ heteroalkyl, $C_6$-$C_{20}$ aryl, $C_6$-$C_{20}$ arylalkyl, $C_3$-$C_{20}$ heteroaryl or $C_6$-$C_{20}$ heteroarylalkyl.

Examples of the alkoxy group which is used as the substituent in the compound of the present invention may include methoxy, ethoxy, propoxy, isobutyloxy, sec-butyloxy, pentyloxy, iso-amyloxy, hexyloxy and the like. At least one hydrogen atom in the alkoxy group may be substituted by the same substituent as defined for the alkyl group.

The aryl group which is used as the substituent in the compound of the present invention refers to a carbocyclic aromatic system including one or more rings, wherein such rings may be attached together in a pendent manner or may be fused. Examples of the aryl group may include aromatic groups such as phenyl, naphthyl, tetrahydronaphthyl, and the like. At least one hydrogen atom of the aryl group may be substituted by the same substituent as defined for the alkyl group (for example, arylamino, arylsilyl, and aryloxy when it is substituted by amino, silyl, and oxy group, respectively).

The heteroaryl group which is used as the substituent in the compounds of the present invention refers to a $C_3$-$C_{30}$ aromatic ring system in which at least one hetero atom selected from N, O, P, and S is included, and the rest of the ring atoms are carbon atoms. The rings may be attached together in a pendent manner or may be fused. At least one hydrogen atom of the heteroaryl group may be substituted by the same substituent as defined for the alkyl group.

Specific examples of the anthracene derivative of Formula 1 as described above may include, but are not limited to, compounds selected from the group consisting of compounds of Formulae 2 to 38:

(Formula 2)

(Formula 3)

-continued (Formula 4)

(Formula 5)

(Formula 6)

(Formula 7)

(Formula 8)

-continued

(Formula 9)

(Formula 10)

(Formula 11)

(Formula 12)

(Formula 13)

(Formula 14)

(Formula 15)

(Formula 16)

(Formula 17)

(Formula 18)

(Formula 19)

(Formula 20)

(Formula 22)

(Formula 23)

(Formula 24)

(Formula 25)

(Formula 26)

(Formula 27)

(Formula 28)

(Formula 29)

(Formula 30)

(Formula 31)

(Formula 32)

(Formula 33)

(Formula 34)

(Formula 35)

(Formula 36)

(Formula 37)

(Formula 38)

Further, the present invention provides an organic electroluminescent device comprising an anode; a cathode; and a layer containing an anthracene derivative of Formula 1 interposed between the anode and the cathode.

The organic electroluminescent device in accordance with the present invention may further comprise at least one layer selected from the group consisting of a hole-injection layer, a hole-transport layer, an electron-transport layer and an electron-injection layer, between the anode and the cathode. These layers serve to facilitate efficient transfer of holes or electrons to light-emitting polymers, thereby heightening the probability of luminescent recombination of electrons and holes in the light-emitting polymers.

The hole-injection layer and the hole-transport layer are stacked to facilitate injection of holes from the anode and transport of the injected holes. A material for the hole-transport layer may include electron-donating molecules having a low ionization potential. For example, there are widely used diamine, triamine or tetramine derivatives which contain triphenylamine as a basic skeleton. There is no particular limit to the materials for the hole-transport layer. Therefore, various materials may be used as the hole-transport layer material, as long as they are conventionally used in the art. For example, mention may be made of N,N'-bis(3-methylphenyl)-N,N'-diphenyl-[1,1-biphenyl]-4,4'-diamine (TPD) or N,N'-di(naphthalen-1-yl)-N,N'-diphenylbenzidine (α-NPD). The organic EL device may further comprise the hole-injection layer (HIL) below the hole-transport layer. There is no particular limit to the materials for the hole-injection layer, as long as they are conventionally used in the art. Examples of the materials for the hole-injection layer include, but are not limited to, compounds of Formulae 39 to 41, e.g. copper phthalocyanine (CuPc) (Formula 39) or starburst-type amine series such as TCTA (Formula 40), m-MTDATA (Formula 41), IDE406 (available from Idemitsu Kosan Co., Ltd, Tokyo, Japan) and the like.

(Formula 39)

(Formula 40)

(Formula 41)

On the other hand, the electron-transport layer effectively transports the electrons supplied from the cathode to a light-emitting layer and inhibits migration of holes which did not recombine with electrons in the light-emitting layer, thereby increasing an opportunity of the electron-hole recombination in the light-emitting layer. There is no particular limit to the materials for the electron-transport layer, as long as they are conventionally used in the art. Examples of materials for the electron-transport layer may include 8-hydroxyquinoline aluminum (Alq3), 2-(4-biphenylyl)-5-(4-t-butylphenyl)-1,3,4-oxadiazole (PBD), 2,4,7-trinitrofluorenone (TNF), BMD, BND, and the like.

Above the electron-transport layer, an electron-injection layer (EIL) may be further stacked which facilitates injection of electrons from the cathode, thereby improving power efficiency. There is no particular limit to the materials for the electron-injection layer, as long as they are conventionally used in the art. Examples of materials for the electron-injection layer may include materials such as LiF, NaCl, CsF, $Li_2O$, BaO and the like.

In addition to the hole-injection layer, hole-transport layer, electron-transport layer and electron-injection layer, the organic EL device in accordance with the present invention may further comprise additional functional stack structures such as a hole-blocking layer and an electron-blocking layer. In this connection, since the inflow of holes into the cathode through the organic light-emitting layer results in decreased lifespan and efficiency of the device, the hole-blocking layer employs a material having a very low HOMO (highest occupied molecular orbital) level in order to prevent such a problem. Even though there is no particular limit to the materials for the hole-blocking layer, they should have an electron transport capacity while an ionization potential higher than that of a luminescent compound. For example, mention may be made of BAlq, BCP, TPBI and the like.

More specifically, organic EL devices having various forms of stack structures are shown in FIGS. 1a to 1e. Referring to FIGS. 1a to 1e, the organic EL device of FIG. 1a has a structure of anode/hole-injection layer/light-emitting layer/cathode, whereas the organic EL device of FIG. 1b has a structure of anode/hole-injection layer/light-emitting layer/electron-injection layer/cathode. Further, the organic EL device of FIG. 1c has a structure of anode/hole-injection layer/hole-transport layer/light-emitting layer/cathode, whereas the organic EL device of FIG. 1d has a structure of anode/hole-injection layer/hole-transport layer/light-emitting layer/electron-injection layer/cathode. Finally, the organic EL device of FIG. 1e has a structure of anode/hole-injection layer/hole-transport layer/light-emitting layer/electron-transport layer/electron-injection layer/cathode.

Meanwhile, even though the organic EL device in accordance with the present invention may include the anthracene derivative in various stack structures disposed between the anode and the cathode, the anthracene derivative may be preferably used as a host material of the light-emitting layer by inclusion of the anthracene derivative in the light-emitting layer between the anode and the cathode.

Hereinafter, a process for preparing the organic EL device in accordance with the present invention will be described in more detail with reference to the accompanying FIGS. 1a to 1e.

First, an anode material is coated on a substrate. As the substrate, a material used in conventional light-emitting devices may be employed. Preferred is a glass substrate or transparent plastic substrate having excellent transparency, surface smoothness, handleability and waterproofness. Further, examples of the anode materials that can be used in the present invention may include materials having transparency and high conductivity conventionally used in the art, such as indium tin oxide (ITO), indium zinc oxide (IZO), tin oxide ($SnO_2$) and zinc oxide (ZnO). The hole-injection layer may be optionally stacked over the anode by a conventional method such as vacuum thermal evaporation or spin coating. Thereafter, the hole-transport layer is formed over the hole-injection layer by vacuum thermal evaporation or spin coating.

Next, the light-emitting layer is stacked over the hole-transport layer over which the hole-blocking layer is then optionally formed by vacuum thermal evaporation or spin coating. Finally, deposition of the electron-transport layer over the hole-blocking layer is carried out by vacuum thermal evaporation or spin coating, followed by optional formation of the electron-injection layer over which a cathode-forming metal is then deposited by vacuum thermal evaporation, thereby fabricating an organic EL device in accordance with the present invention. Examples of the cathode-forming metal that can be used in the present invention may include lithium (Li), magnesium (Mg), aluminum (Al), aluminum-lithium (Al—Li), calcium (Ca), magnesium-indium (Mg—In), magnesium-silver (Mg—Ag) and the like. In order to obtain a top-emitting device, a transmission cathode using ITO or IZO may be employed.

EXAMPLES

Now, the present invention will be described in more detail with reference to the following examples. These examples are provided only for illustrating the present invention and should not be construed as limiting the scope and spirit of the present invention.

Synthesis Example 1

Preparation of Inventive Anthracene Derivative(2,7,9,10-tetraphenylanthracene)

1-1. Synthesis of 2,7-dibromo-9,10-dihydroxy-9,10-diphenylanthracene 2,7-dibromo-9,10-dihydroxy-9,10-diphenylanthracene was synthesized according to Reaction Scheme 1 below.

Reaction Scheme 1

The above reaction was carried out as follows.

39.6 mL (0.38 mol) of bromobenzene and 520 mL of THF were placed in a 1 L round bottom flask and cooled to −78° C. Then, 205.6 mL (0.33 mol) of n-butyllithium was gradually added dropwise thereto, and the mixture was stirred at that temperature for 30 min, followed by addition of 34.4 g (0.09 mol) of 2,7-dibromoanthraquinone. The reaction material was elevated to room temperature and stirred overnight, and 260 mL of 2N hydrochloric acid was added thereto. The resulting mixture was subjected to phase separation and the thus-obtained organic layer was dried over MgSO$_4$, followed by filtration and concentration for a subsequent reaction.

1-2. Synthesis of 2,7-dibromo-9,10-diphenylanthracene 2,7-dibromo-9,10-diphenylanthracene was synthesized according to Reaction Scheme 2 below.

Reaction Scheme 2

The above reaction was carried out as follows.

2,7-dibromo-9,10-dihydroxy-9,10-diphenylanthracene obtained in Reaction Scheme 1 was placed in a 500 mL round bottom flask to which 46.8 g (0.28 mol) of KI, 49.6 g (0.56 mol) of NaH$_2$PO$_2$—H$_2$O and 350 mL of acetic acid were then added, followed by reflux cooling for 3 hours. The resulting mixture was cooled to room temperature, filtered, and washed with excessive water and methanol. The washed material was dried, and recrystallized from toluene to give solids. The solids were filtered, and dried under reduced pressure to afford 33.1 g of 2,7-dibromo-9,10 diphenylanthracene (yield of 72.1% based on bromobenzene in Reaction Scheme 1 of Synthesis Example 1).

1-3. Synthesis of 2,7,9,10-tetraphenylanthracene

According to Reaction Scheme 3 below, an anthracene derivative in accordance with the present invention, i.e., 2,7,9,10-tetraphenylanthracene was synthesized.

Reaction Scheme 3

The above reaction was carried out as follows.

Figure 1A:
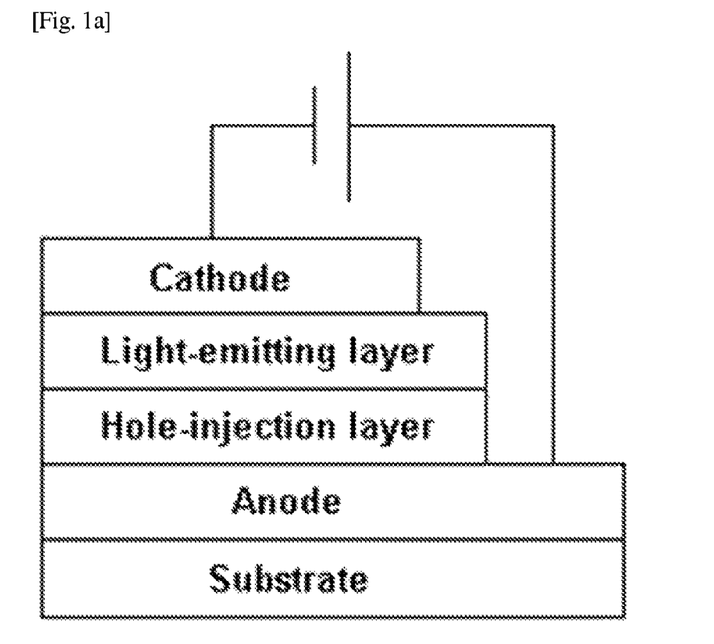
FIGS. 1a to 1e are sectional views showing stack structures of organic electroluminescent devices in accordance with preferred embodiments of the present invention.
Figure 1B:
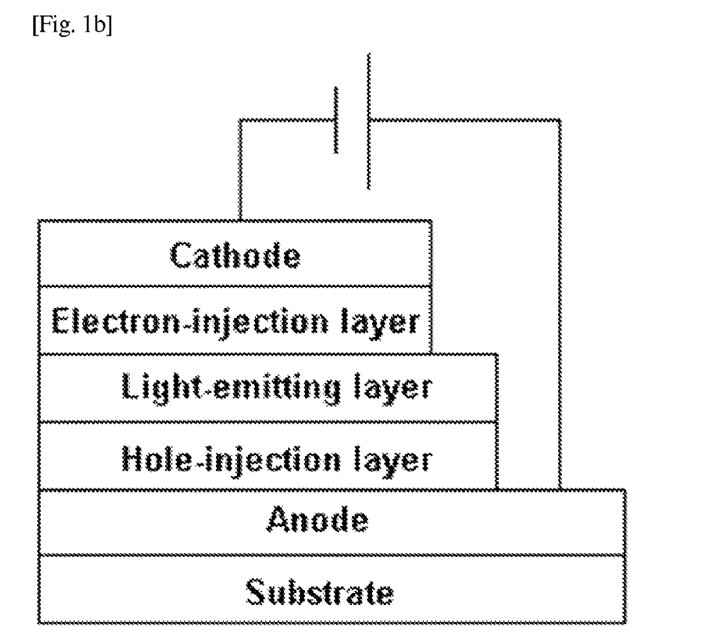
Figure 1C:
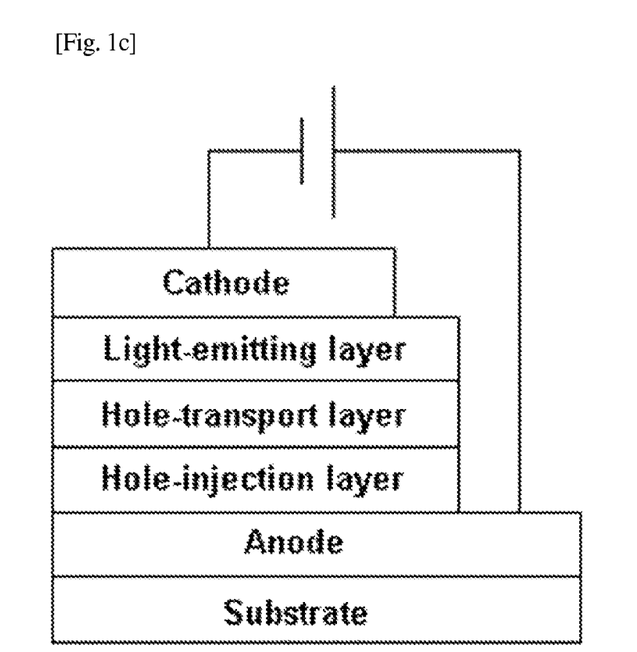
Figure 1D:
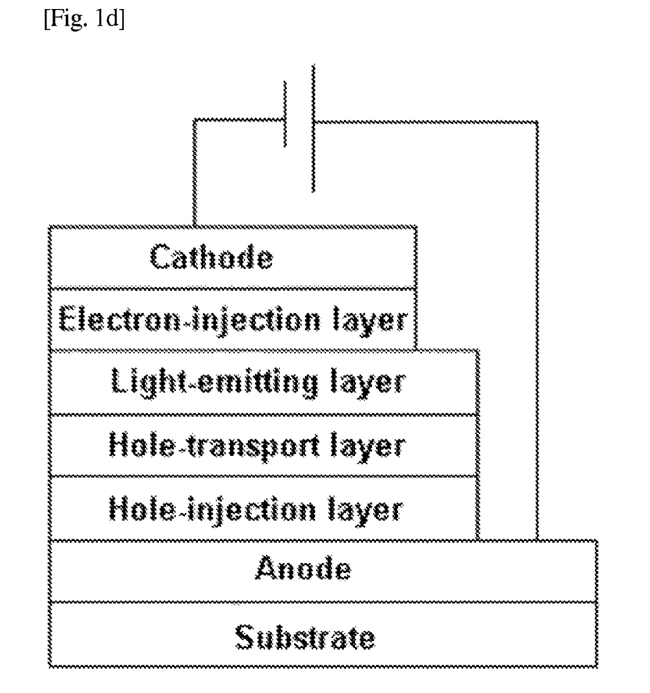
Figure 1E:
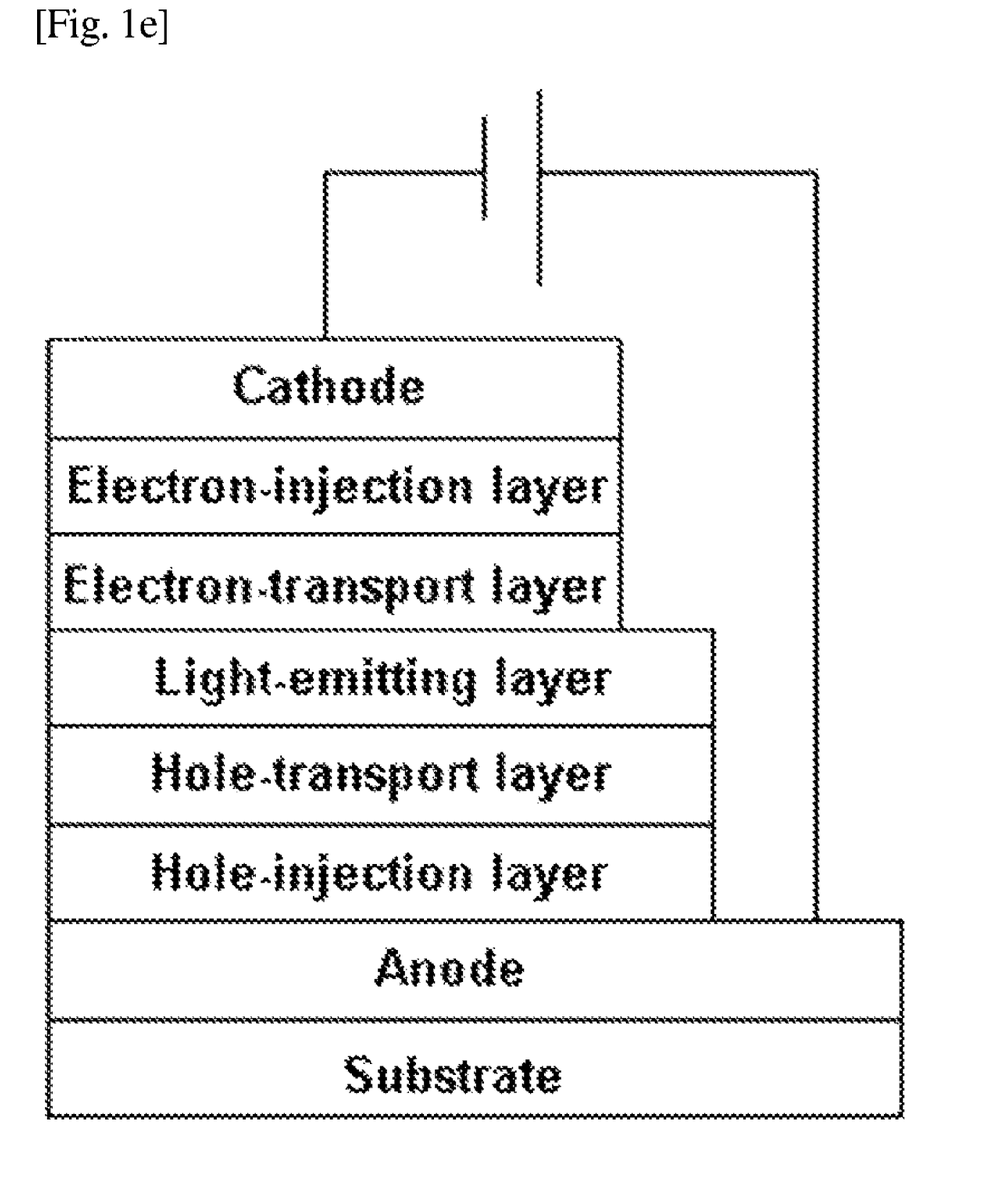
Figure 2:
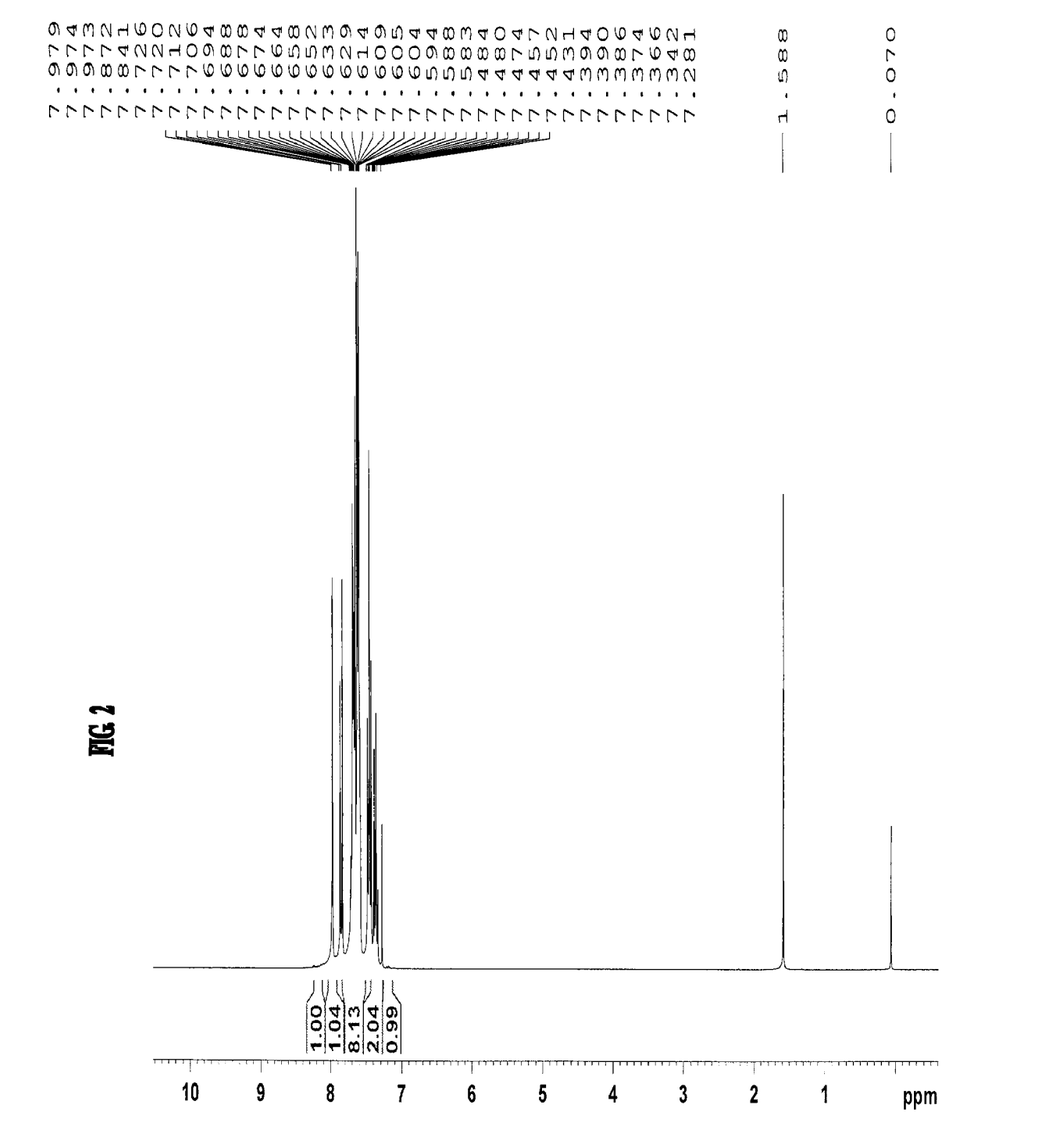
FIG. 2 shows a $^1$H-NMR spectrum of an anthracene derivative of the present invention prepared according to Synthesis Example 1.

11.0 g (0.023 mol) of 2,7-dibromo-9,10-diphenylanthracene obtained in Reaction Scheme 2, 8.4 g (0.069 mol) of 4-phenylboric acid, 10.4 g (0.076 mol) of potassium carbonate, 1.4 g (0.001 mol) of Pd(PPh$_3$)$_4$, 40 mL of water, 150 mL of toluene and 15 mL of THF were placed in a 1 L round bottom flask, and reacted under reflux cooling for 24 hours. After the reaction was completed, the reaction product was cooled to room temperature, and filtered while washing with methylene chloride. The filtrate was subjected to phase separation, and the thus-obtained organic layer was washed three times with water, concentrated under reduced pressure and subjected to column separation using methylene chloride. The solution was concentrated under reduced pressure, precipitated in methanol, and filtered while washing with methanol. The filtrate was dried under reduced pressure to afford 4.7 g of 2,7,9,10-tetraphenylanthracene (yield: 42.0%, HPLC 99.7%, m.p. 262.2° C.). The $^1$H-NMR spectrum for the desired product is shown in FIG. 2.

Synthesis Example 2

Preparation of inventive anthracene derivative(2,7-di(4'-biphenyl)-9,10-diphenylanthracene)

Analogous to the procedure described in Synthesis Examples 1-1 and 1-2, 2,7-dibromo-9,10-diphenylanthracene was synthesized. Then, the anthracene derivative in accordance with the present invention, i.e. 2,7-di(4'-biphenyl)-9,10-diphenylanthracene was synthesized according to Reaction Scheme 4 below.

Reaction Scheme 4

The above reaction was carried out as follows.

Figure 3:
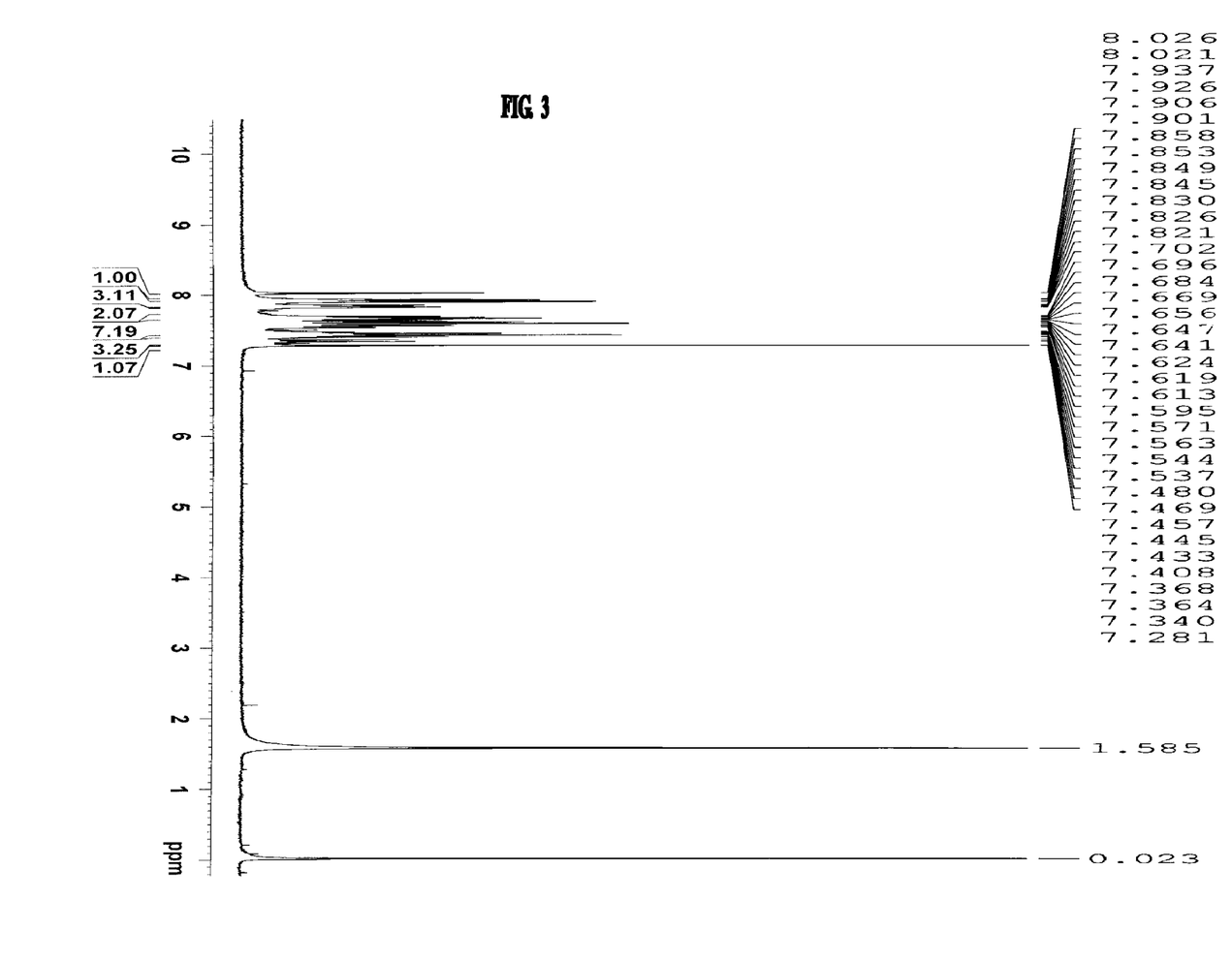
FIG. 3 shows a $^1$H-NMR spectrum of an anthracene derivative of the present invention prepared according to Synthesis Example 2.

11.0 g (0.023 mol) of 2,7-dibromo-9,10-diphenylanthracene obtained in Section 1-2, 13.7 g (0.069 mol) of 4-biphenylboric acid, 10.4 g (0.076 mol) of potassium carbonate, 1.4 g (0.001 mol) of Pd(PPh$_3$)$_4$, 40 mL of water, 150 mL of toluene and 15 mL of THF were placed in a 1 L round bottom flask, and reacted under reflux cooling for 24 hours. After the reaction was completed, the reaction product was cooled to room temperature, and filtered while washing with methylene chloride. The filtrate was subjected to phase separation, and the thus-obtained organic layer was washed three times with water, concentrated under reduced pressure and subjected to column separation using methylene chloride. The solution was concentrated under reduced pressure, precipitated in methanol, and filtered while washing with methanol. The filtrate was dried under reduced pressure to afford 5.8 g of 2,7 di(4'-biphenyl)-9,10-diphenylanthracene (yield: 39.4%, HPLC 99.7%, m.p. 329.1° C.). The $^1$H-NMR spectrum for the desired product is shown in FIG. 3.

Example 1

Fabrication of Organic EL Device According to a Preferred Embodiment of the Present Invention The ITO glass substrate was patterned to have a light-emitting area of 2 mm×2 mm and then cleaned. The substrate was mounted in a vacuum chamber which was then adjusted to a base pressure of 1×10⁶ torr. Using a known method, films of CuPC (200 Å), NPD (400 Å), a compound prepared in Synthesis Example 1+C545T (5%) (200 Å), Alq$_3$ (350 Å), LiF (5 Å), and Al (1000 Å) were sequentially formed on the ITO glass. The thus-fabricated organic EL device exhibited luminance of 1839 Cd/m² (6.61 V) at 0.4 mA.

Example 2

Fabrication of Organic EL Device According to Another Preferred Embodiment of the Present Invention An organic EL device was fabricated in the same manner as in Example 1, except that a compound prepared in Synthesis Example 2 was used instead of a compound prepared in Synthesis Example 1. The thus-fabricated organic EL device exhibited luminance of 1485 Cd/m (6.18 V) at 0.4 mA.

Comparative Example 1

Fabrication of a Prior Art Organic EL Device

An organic EL device was fabricated in the same manner as in Example 1, except that 9,10-di(2-naphthyl)anthracene was used instead of a compound prepared in Synthesis Example 1. The thus-fabricated organic EL device exhibited luminance of 1048 Cd/m² (5.65 V) at 0.4 mA.

Various properties of the organic EL devices of Examples 1 and 2 and Comparative Example 1 are summarized in Table 1 below.

TABLE 1

| Example No. | Voltage (V) | Current (mA) | Current Efficiency (Cd/A) | Power Efficiency (lm/W) | Luminance (Cd/m²) | Color Coordinate (CIEx) | Color Coordinate (CIEy) | Lifespan (h) |
|---|---|---|---|---|---|---|---|---|
| Comp. Ex. 1 | 5.65 | 0.4 | 10.48 | 5.8284 | 1048 | 0.3135 | 0.6462 | 89 |
| Ex. 1 | 6.61 | 0.4 | 18.39 | 8.7436 | 1839 | 0.3058 | 0.6537 | 382 |
| Ex. 2 | 6.18 | 0.4 | 14.85 | 7.5475 | 1485 | 0.3175 | 0.6457 | 496 |

Referring to Table 1, it can be seen that the organic EL devices of Examples 1 and 2 exhibited excellent power and luminance efficiencies and a long service life, as compared to the organic EL device of Comparative Example 1.

As apparent from the above description, the present invention can provide an organic electroluminescent (EL) device having excellent power and luminance efficiencies in conjunction with a long service life.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. An organic electroluminescent device comprising an anode; a cathode; and a layer containing an anthracene derivative interposed between the anode and the cathode, wherein the anthracene derivative is a compound selected from the group consisting of compounds of Formulae 2 to 16:

(Formula 2)

(Formula 3)

-continued

(Formula 4)

(Formula 5)

(Formula 6)

(Formula 7)

(Formula 8)

(Formula 9)

(Formula 10)

(Formula 11)

(Formula 12)

(Formula 13)

(Formula 14)

(Formula 15)

and (Formula 16)

.

2. The organic electroluminescent device according to claim 1, further comprising at least one layer selected from the group consisting of a hole-injection layer, a hole-transport layer, a hole-blocking layer, an electron-transport layer, an electron-injection layer and an electron-blocking layer, between the anode and the cathode.

3. The organic electroluminescent device according to claim 1, wherein the anthracene derivative is included in a light-emitting layer between the anode and the cathode.

* * * * *